(12) United States Patent
Burch

(10) Patent No.: US 8,122,755 B2
(45) Date of Patent: Feb. 28, 2012

(54) METHOD FOR EVALUATING HIGH TEMPERATURE WEAR LIFE

(75) Inventor: Robert Ray Burch, Exton, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 201 days.

(21) Appl. No.: 12/544,590

(22) Filed: Aug. 20, 2009

(65) Prior Publication Data

US 2010/0043522 A1 Feb. 25, 2010

Related U.S. Application Data

(60) Provisional application No. 61/189,632, filed on Aug. 20, 2008.

(51) Int. Cl.
*G01N 3/56* (2006.01)
*G01N 19/02* (2006.01)
*G01N 3/60* (2006.01)
*G01N 17/00* (2006.01)

(52) U.S. Cl. .............................................. 73/7; 374/57

(58) Field of Classification Search ................ 73/7, 374; 374/57

See application file for complete search history.

(56) References Cited

U.S. PATENT DOCUMENTS 4,360,626 A 11/1982 Manwiller
(Continued)

FOREIGN PATENT DOCUMENTS

DE 102004048028 A1 4/2006

OTHER PUBLICATIONS de Bauijn, J.C.M. et al., "The Design and Application of a Microfoil Tensile Test Apparatus for Monitoring the Degree of Ultraviolet Degradation of Polymers", Review of Scientific Instruments, Jun. 1991, pp. 1620-1623, vol. 62, New York, USA.

(Continued)

*Primary Examiner* — Lisa Caputo
*Assistant Examiner* — Roger Hernandez-Prewitt
(74) *Attorney, Agent, or Firm* — Chyrrea J. Sebree

(57) ABSTRACT

A method is provided for evaluating relative wear life polymeric specimens intended for use at high temperature under high wear conditions.

3 Claims, 4 Drawing Sheets

U.S. PATENT DOCUMENTS

| | | |
|---|---|---|
| 4,957,012 A | 9/1990 | Cuddihy et al. |
| 2002/0037944 A1* | 3/2002 | Shen et al. .................... 522/153 |
| 2004/0156879 A1* | 8/2004 | Muratoglu et al. ........... 424/423 |
| 2005/0268734 A1 | 12/2005 | Watkins, Jr. et al. |
| 2007/0240528 A1 | 10/2007 | Kranbuehl |

OTHER PUBLICATIONS

Bryant, R.G., "Polyimides", Encyclopedia of Polymer Science and Technology, 3rd Edition, pp. 529-554, vol. 7, 2003, J.I. Kroschwitz ed., Published by John Wiley & Sons, Inc., Hoboken, New Jersey.

* cited by examiner

METHOD FOR EVALUATING HIGH TEMPERATURE WEAR LIFE

CROSS-REFERENCE TO RELATED APPLICATIONS

This application claims the benefit of U.S. Provisional Application No. 61/189,632, filed Aug. 20, 2008, which is incorporated herein by reference in its entirety.

FIELD OF THE INVENTION

The disclosure relates to a method for determining relative wear life of polymeric specimens, and more particularly, polyimide specimens, and parts intended for use at high temperature under high wear conditions or in a chemically corrosive environment under high wear conditions.

TECHNICAL BACKGROUND OF THE INVENTION

Applications requiring high wear resistance, particularly at conditions of high temperature, pressure, velocity and/or chemically degrading or corrosive, require materials that can perform for long times under stress and at high temperatures. In the aerospace market, examples of such applications are aircraft engine parts and aircraft wear pads. In the automotive market, examples of such applications are automatic transmission bushings and seal rings, tenter frame pads and bushings, material processing equipment parts, and pump bushings and seals.

Typically, a component in applications as described above is intended to function as a sacrificial, or consumable, component, preventing or reducing the wear or damage that a more costly mating or adjacent component would experience if it were mated against some other component over time under stress or oxidative stress. A component loses efficacy as a sacrificial wear reducer. However, as the component wears, the resulting increased clearances can result in deleterious effects, such as increased leakage (of air pressure or fluid) or increased noise, thereby reducing the operating effectiveness of the entire system in which the worn component is contained. Ultimately it loses its ability to prevent or reduce the wear or damage to a more costly mating or adjacent component. Restoring the system to its original operating effectiveness would require replacement of the worn component with a new un-used component. Replacement may require disassembly, reassembly, testing and re-calibration ("service") of the system, resulting in considerable costs in terms of downtime and labor. Thus, a component that demonstrates a lower rate of wear is desirable to reduce the frequency of replacement, thereby reducing cost.

When choosing among candidate materials for a particular application, it would be useful to predict which candidate is most likely to yield parts with the longest wear life. Evaluating and comparing the wear life of parts made of different materials, or made of the same material in different manners, for these high temperature, high wear applications is difficult. Practitioners in this field typically use wear rate, such as described in the ASTM standard G133, and, where applicable, thermal oxidative stability (TOS) measurements to compare two materials.

A limitation of the thermal oxidative stability test is that it provides information on weight loss over time at temperature but does not provide direct information on wear life at temperature. Designers of jet engines draw inferences from the TOS information, reasoning that the higher the weight loss in the VV TOS test, the shorter the life time at temperature is likely to be. Likewise, wear tests provide information for designers on the wear rate of materials but only over limited periods of time, forcing designers to draw inferences about changes in wear rate as a function of time at temperature. However, the relationship among wear rate, thermal oxidative stability, and wear life is not well-defined. It is possible for two materials to have similar thermal oxidative stability values and similar wear rates as determined by ASTM G133 but very different wear life or lifetimes. Other practitioners thermally age parts or specimens made of the materials of interest and then measure the change in mechanical properties. Still others thermally age materials and then measure the change in thermal oxidative stability values. Neither of these approaches provides a direct comparison of wear life.

There remains a need for a convenient method that provides a direct, reliable comparison of the relative wear life of materials intended for use in applications requiring high wear resistance at high temperatures.

BRIEF DESCRIPTION OF THE DRAWINGS

Various features and/or embodiments of this invention are illustrated in drawings as described below. These features and/or embodiments are representative only, and the selection of these features and/or embodiments for inclusion in the drawings should not be interpreted as an indication that subject matter not included in the drawings is not suitable for practicing the invention, or that subject matter not included in the drawings is excluded from the scope of the appended claims and equivalents thereof.

SUMMARY OF THE INVENTION

Figure 1:
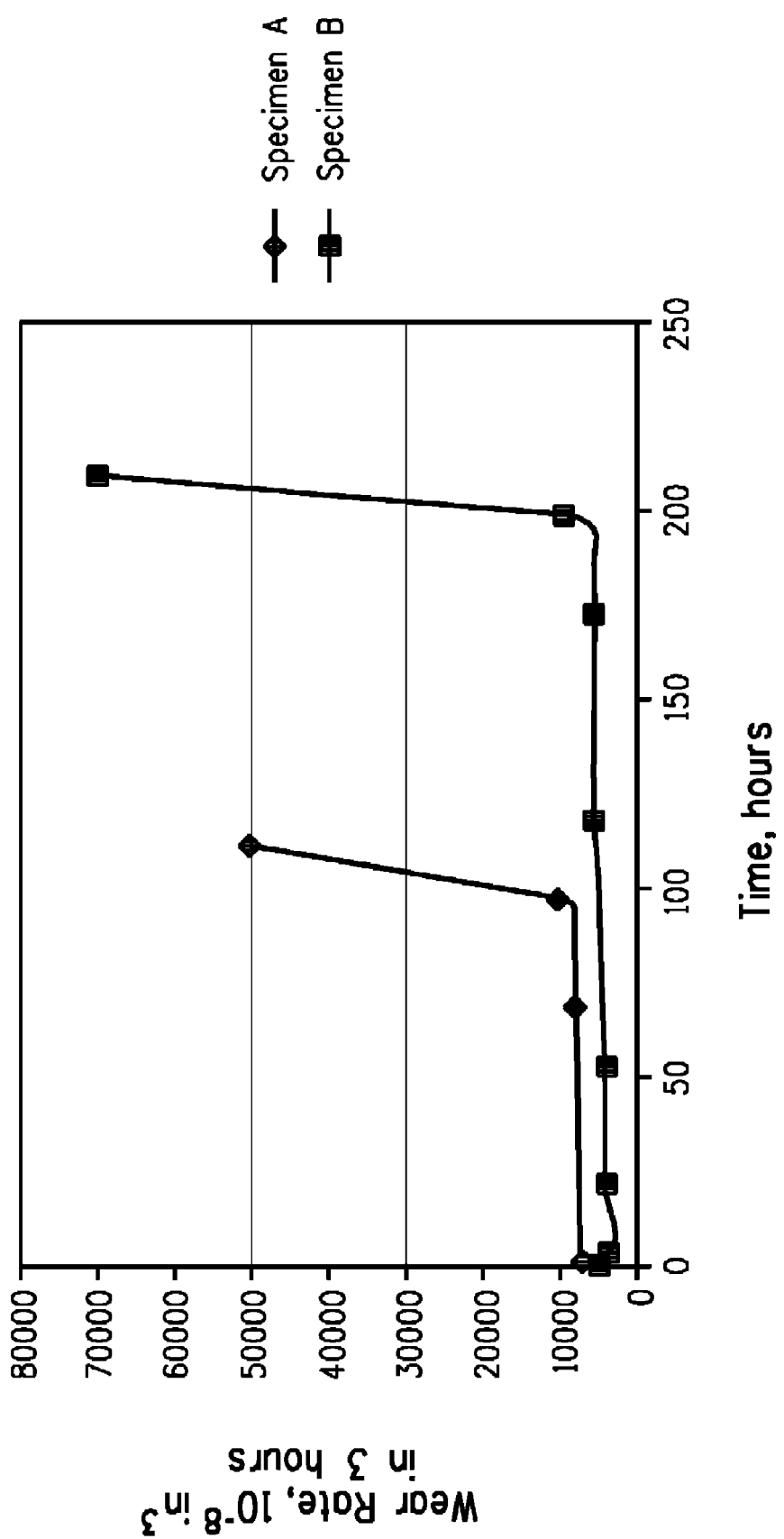
FIG. 1 is a graph of wear rate versus aging time at 800° F. (427° C.) in air for two different Polymeric Specimens, A and B.

Disclosed herein is a method for evaluating relative wear life of a polymeric specimen, comprising:

a) providing at least two sets of polymeric specimens, wherein
   (i) each specimen within each set is made of same composition and in same manner, or
   (ii) each specimen within each set is made of same composition as at least one other set and made in a different manner; or
   (iii) each specimen within each set is made of different composition as at least one other set and made in same manner; or
   (iv) each specimen within each set is made of a different composition as at least one other set and made in different manner;

b) determining wear rate as a function of aging time for each set, by:
   (i) reserving at least one specimen as an unaged control;
   (ii) aging each remaining specimen by heating under a specified atmosphere and at specified temperature for a specified aging time;

(iii) measuring the wear rate of the unaged and aged specimens over time;

c) comparing the wear rates as determined in step (b) for each set of specimens.

DETAILED DESCRIPTION OF THE INVENTION

The methods described herein provide a convenient way to evaluate the relative performance, under high temperature, high wear conditions, of polymeric specimens or parts made of the same or different polymeric materials and/or prepared differently,. An evaluation of such materials is useful to help one predict the performance of polymeric materials when applied for its intended use.

Materials suitable for use in the methods described herein are filled and unfilled high-temperature polymers, selected from the group consisting of polyimide, a polyetherimide, a polyketone (e.g., polyetheretherketone and polyetherketoneketone), a polybenzoxazole, a polybenzimidazole, a polyaramide, a polyarylene, a polyether sulfone, a polyarylene sulfide, a polyimidothioether, a polyoxamide, a polyimine, a polysulfonamide, a polysulfonimide, a polyimidine, a polypyrazole, a polyisoxazole, a polythiazole, a polybenzothiazole, a polyoxadiazole, a polytriazole, a polytriazoline, a polytetrazole, a polyquinoline, a polyanthrazoline, a polypyrazine, a polyquinoxaline, a polyquinoxalone, a polyquinazolone, a polytriazine, a polytetrazine, a polythiazone, a polypyrrone, a polyphenanthroline, a polycarbosilane, a polysiloxane, a polyamideimide, and copolymers or blends thereof.

The unique performance of polymeric materials under stress, and particularly, polyimide compositions under stress and at high temperatures have made them particularly useful in such applications. As used herein, the term "polyimide" denotes a polymer in which at least about 80% of the linking groups between repeat units are imide groups, —CONRCO—. The synthesis and properties of polyimides is reviewed by, for example, R. G. Bryant, in "Polyimides," *Encyclopedia of Polymer Science and Technology*, 3rd ed., J. I. Kroschwitz ed., vol. 7, pp. 529-554).

In addition to the polymeric material, additives may be present in the specimen to be tested. For instance, an illustrative, and non-exclusive list of additives that may be present are: pigments, antioxidants, materials to control the coefficient of thermal expansion, lubricious and/or nonlubricious fillers, etc. Examples of these additives include graphite, kaolinite, $TiO_2$, hindered phenols, polytetrafluoroethylene (PTFE), boron nitride (BN), etc.

The method disclosed herein includes a method for determining the wear of a polymeric specimen or polymeric part as a function of aging time at a specified temperature. For polymers that are infusible, specimens for testing may be made from them by the application of heat and pressure to powder mixtures of the various ingredients in the composition of interest. See, for instance, U.S. Pat. No. 4,360,626. These powder mixtures may be made by simple blending of powders. Inorganic powder components may be added to the synthetic process for making the polyimide polymer, to obtain mixture of the polymer and other ingredients. If the polymer is thermoplastic, test specimens or test parts may be formed by melt forming methods, such as extrusion or injection molding, which are typically used to form thermoplastic parts.

In the methods described herein, for each defined state of interest (e.g., composition, manner of preparation, post treatment etch), several shaped parts or specimens are made as test samples. Test samples can be of the cylindrical shape of ASTM G133, or they can be, for example, tensile bars.

In the methods disclosed herein, the wear performance of the test specimens is determined by comparing unaged polymer specimen sets to aged polymer specimen sets that have been subjected to certain conditions At least one specimen is included in each set, but one may use as many specimens in each set as one chooses. At least one set of polymeric specimens is reserved as an unaged control, while the remaining sets of specimens or parts are aged by heating at a specified temperature for specified lengths of time and a specified atmosphere This is conveniently accomplished for example, by putting all specimens or parts to be aged in an oven at temperature and withdrawing them in turn at designated aging times. The choice of temperature, atmosphere, and aging times will depend on the nature of the application of interest. For example, specimen representing materials or shapes of parts intended for aerospace applications may be aged for 1 to 300 hours or more in air at temperatures in the range of 750 to 900° F. (399 to 482° C.). The aging time preferably should be long enough to induce a change in wear rate that is at least about 3 times the standard deviation of the wear rate measurement.

After the test samples have been aged, the wear rate is determined for each. The specific wear test used will depend on the nature of the application for which the material is intended and on the geometry of the specimen. For example, a wear tester that uses a polymer block on a spinning metal ring is suitable for automotive applications, while tests for aerospace applications generally operate in oscillatory mode and have temperature control. A test used by a manufacturer in the field may be performed for long times on, for example, actual sintered bushings. ASTM G 133-05 (2005), "Standard Test Method for Linearly Reciprocating Ball-on-Flat Sliding Wear", includes useful laboratory procedures for determining the sliding wear of ceramics, metals, and other candidate wear-resistant materials using a linear, reciprocating ball (for example, a steel ball)-on-flat plane geometry.

One example of a commercially available tester is sold by Bud Labs, Inc., (Rochester, N.Y.) and implements a modified version of ASTM G133. It involves oscillatory wear of a 3/8" (0.95 cm) diameter metal ball of either chrome steel (AISI E52100 high carbon steel, Rockwell hardness 64) or titanium on a 1" (2.5 cm) diameter specimen that is approximately 0.5 cm thick. In typical operation, the ball is mounted on an arm that imposes a 2 lb (0.91 kg) weight on the test specimen, and the arm is oscillated at 300 cycles /min for 54000 cycles (3 hours). The ball and test specimen are pre-heated to the test temperature in an oven, and the assembly is maintained in an oven for the duration of the test. The test yields a force vs. time plot, from which an approximation of the coefficient of friction can be estimated. The volume of the wear scar is measured at the end of the experiment. The volume may be measured, for example, by stylus profilometry or optical profilometry. The wear rate is then the volume divided by the test time, here, 3 hours. Visual inspection of the test specimens sometimes, but not always, reveals flaking, cracking, pitting, or other modes of failure near the end of the effective period of wear resistance for a given composition.

Figure 2:
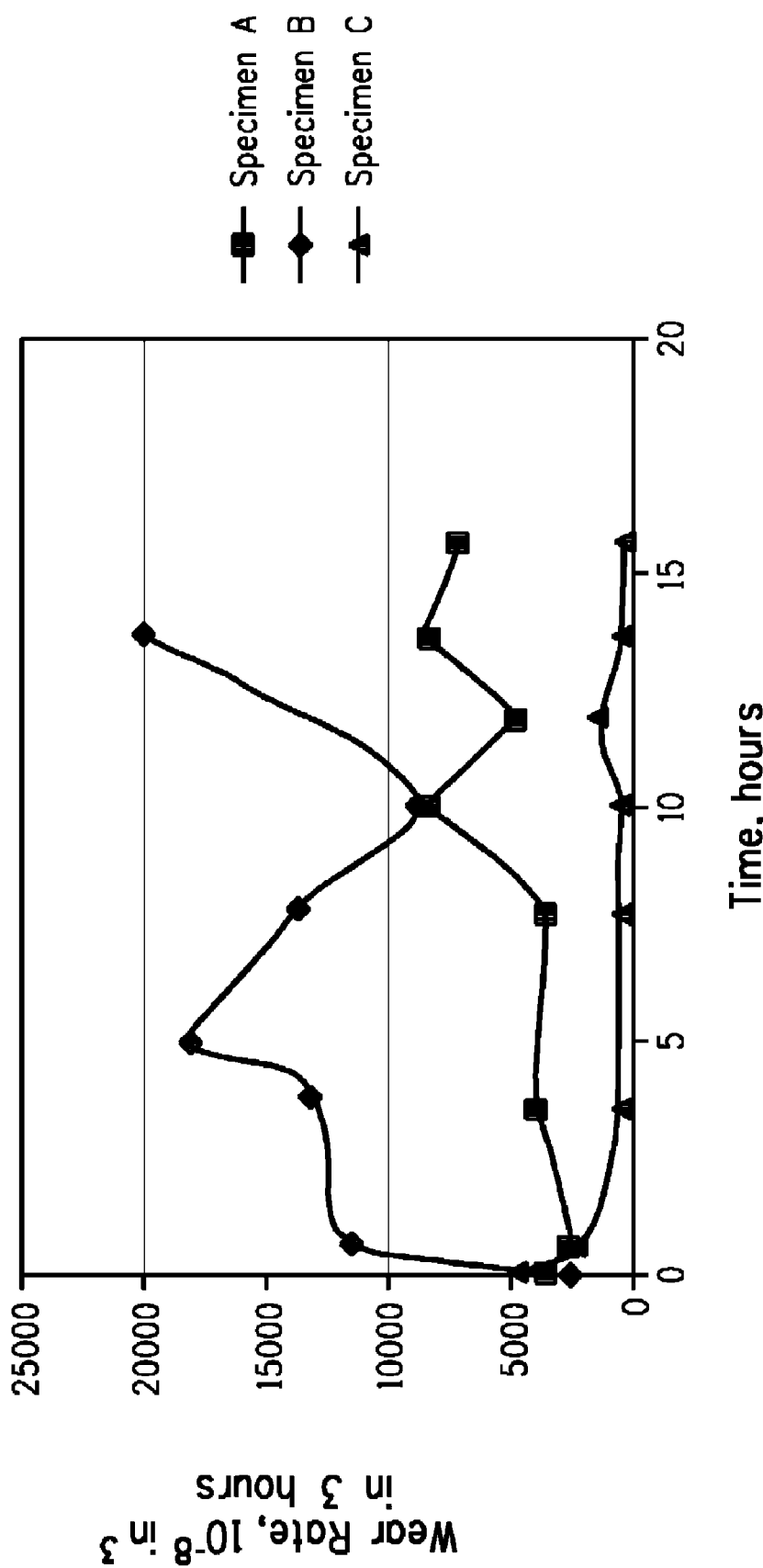
FIG. 2 is a graph of wear rate versus aging time at 900° F. (482° C.) in air for three different Polymeric Specimens, A, B and C.

Once the wear rates have been determined, they are plotted as a function of the aging time, one curve for each defined state. The curves are then compared to each other to predict expected relative performance in the application or intended use of the polymeric material or part.

Where a curve has a "hockey stick" shape as in FIG. 1 the relative wear life can be identified by visual inspection as the aging time at which the wear rate sharply increases. This sharp increase indicates catastrophic failure of the part. More generally, a relative wear life or lifetime can be identified as an aging time beyond which the wear rate is greater than about 3 times the standard deviation of the wear rate measurement. For the data in FIG. 1, the relative life for the test specimens made of compositions POLYMERIC SPECIMEN A and POLYMERIC SPECIMEN B are about 90 and about 180 hours, respectively, at 800° F. (427° C.) in air.

Where the plot of wear rate versus aging time is a curve that does not have a "hockey stick" shape, for example, as in FIG. 2, it is more useful to assess relative performance by comparing the area under each curve, a larger area indicating poorer performance. Often, this can be assessed by visual inspection. In FIG. 2, the area under the curve for Polymeric Specimen B is clearly larger than the area under the curve for polyimide composition Polymeric Specimen A, which in turn is larger than the area under the curve for polyimide composition Polymeric Specimen C. Thus, the performance of parts or shaped specimens made of Polymeric Specimen B are expected to perform more poorly in high wear conditions at 900° F. (482° C.) in air than parts or shaped specimens made of Polymeric Specimen A, which in turn are expected to perform more poorly than part made of Polymeric Specimen B.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

Materials.

"BPDA" means 3,3',4,4'-biphenyltetracarboxylic dianhydride.

"MPD" means -m-phenylene diamine.

"PPD" means p-phenylene diamine,

"PMDA" means pyromellitic dianhydride.

"ODA" means diaminodiphenyl ether.

Polymeric Specimen A is a polyimide prepared from BPDA and PPD which contains 2.5 wt % graphite.

Polymeric Specimen B is a polyimide prepared from BPDA and a 70/30 ratio of PPD/MPD which contains 50 wt % graphite.

Polymeric Specimen C is a polyimide prepared from BPDA and a 70/30 ratio of PPD/MPD which contains 9 wt % graphite and 1 wt % kaolinite.

Polymeric Specimen D is a polyimide prepared from BPDA and a 70/30 ratio of PPD/MPD.

Polymeric Specimen E is a polyimide prepared from PMDA and ODA which contains 30 wt % graphite.

Each of Polymeric Specimens A, B, C, D and E were obtained from E.I. du Pont de Nemours & Co., Inc. (Wilmington, Del., USA). Polymeric Specimens C and D exemplify the disclosed method for unfilled polymeric specimens. Polymeric Specimens A, B and E exemplify the disclosed method for filled polymeric specimens.

Methods.

Test sample fabrication. A polymeric specimen prepared from dried polyimide resin was fabricated into disks 1" (2.5 cm) in diameter and about 0.5 cm thick by direct forming, using a procedure substantially according the procedure described in U.S. Pat. No. 4,360,626 (especially column 2, lines 54-60) and Tensile bars were prepared by the method set forth in U.S. Pat. No. 4,360,626, which is incorporated herein by reference in its entirety.

Heat aging method. The bars were randomly placed on a stainless steel wire mesh rack within a Thermolyne 1300 muffle furnace (Barnstead International, Dubuque, Iowa, USA, part of Thermo Fisher Scientific, Inc., Waltham, Mass., USA). The furnace was modified to include an inlet and outlet such that air or nitrogen purge can be supplied. After sample placement, the furnace was closed and purged with nitrogen (10 to 15 scfh, 0.28 to 0.42 m$^3$/h flow rate) for 30 minutes before heating was started. While under nitrogen the furnace was heated to 350° C. over a 3 to 6 hour period. The furnace temperature was held at 350° C. for 3 to 16 hours. The furnace was then heated to the desired test temperature with monitoring as measured by a thermocouple placed at the center on the middle shelf of the wire mesh rack. The test temperature was maintained while under nitrogen for 0 to 30 minutes, before switching to air (10 to 15 scfh, 0.28 to 0.42 m$^3$/h flow rate). Time zero was defined as the time at which air was switched on. Disks were removed from the furnace at various intervals and placed in a nitrogen-purged enclosure to cool.

Zone temperatures in the furnace were monitored at varying positions during the course of the tests. A two percent variability in temperature was observed from the top to the bottom of the furnace with the top and sides of the furnace chamber generally being hotter than the bottom and the door face. This variation depended on the number of disks in the furnace. It was necessary to always monitor zone temperatures in the oven and to shuffle the positions of the disks such that all disks were exposed to the variable zones during the course of the aging study, to ensure uniform thermal oxidative exposure.

Wear rates were determined using a modified version of ASTM G133. It involved oscillatory wear of a ⅜" (0.95 cm) diameter metal ball of either chrome steel (AISI E52100 high carbon steel, Rockwell hardness 64) on the test specimen. The ball was mounted on an arm that imposed a 2 lb (0.91 kg) weight on the test specimen, and the arm was oscillated at 300 cycles/min for 54000 cycles (3 hours). The ball and test specimen were pre-heated to the test temperature in an oven, and the assembly was maintained in an oven for the duration of the test. The volume of the wear scar was measured at the end of the experiment by means of an optical profilometer (ZYGO Corporation, Middlefield, Conn., USA) or alternatively by stylus profilometry. In these examples, the wear volume is taken as the wear rate over a three hour interval. The standard deviation of the wear measurement depended to a small degree on the specific polyimide composition tested but was typically about 2 to 8% of the wear rate.

Although the data presented in these Examples was collected using the ASTM G133 wear tester, it is reasonable to assume that a similar experiment conducted with other methods of evaluating wear would produce similar results. This includes pin-on-disk testing.

Example 1

Cylindrically shaped disks, 1 inch (2.5 cm) diameter×0.5 cm thickness, of polymeric specimens A and B were aged in air at 800° F. (427° C.). Wear rates were measured on unaged and aged samples and are presented in Table 1 and plotted versus aging time in FIG. 1. The plot in FIG. 1 indicates that, for Specimen B and the wear rate remain fairly small until about 180 hours. At this point, thermal oxidative degradation is taking place at a significant rate, and the test specimen is losing structural integrity such that its wear rate accelerates dramatically. The "hockey stick" appearance of the curves is typical. It is probably reasonable to assume that, in the hypothetical situation in which an engine bushing made of Specimen B is held continuously at 800° F. (427° C.) in an engine in the field, we would expect it to last for about 180 hours. This can be thought of as saying that thermal oxidative stability limits the wear life to about 180 hours at 800° F. (427° C.). Similarly, in the hypothetical situation in which an engine bushing made of Specimen A is held continuously at 800° F. (427° C.) in an engine in the field, we would expect it to last for only about 90 hours.

TABLE 1

| POLYMERIC SPECIMEN | Aging Time at 800° F. (hours) | Wear Rate ($10^{-8}$ $in^3$) |
|---|---|---|
| B | 0 | 4305 |
|   | 4 | 3280 |
|   | 24 | 3995 |
|   | 56 | 3995 |
|   | 120 | 6150 |
|   | 168 | 6150 |
|   | 197 | 8405 |
|   | 216 | 69085 |
|   | 288 |   |
| A | 0 | 6286 |
|   | 72 | 7857 |
|   | 96 | 9914 |
|   | 120 | >50000 |
|   | 144 |   |
|   | 171 |   |

Example 2

Cylindrically shaped disks, 1 inch (2.5 cm) diameter×0.5 cm thickness, Specimens B, A, and C were aged in air at 900° F. (482° C.). Wear rates were measured on unaged and aged samples and are presented in Table 2 and plotted versus aging time in FIG. 2.

In FIG. 2, the area under the curve for polyimide composition Specimen B is clearly larger than the area under the curve for polyimide composition Specimen A, which in turn is larger than the area under the curve for polyimide composition Specimen C. Thus, the performance of parts or shaped specimens made of Specimen B are expected to perform more poorly in high wear conditions at 900° F. (482° C.) in air than parts or shaped specimens made of Specimen A, which in turn are expected to perform more poorly than parts or shaped specimens made of Specimen B.

TABLE 2

| POLYMERIC SPECIMEN | Aging Time at 900° F. (hours) | Wear Rate ($10^{-8}$ $in^3$) |
|---|---|---|
| B | 0 | 2255 |
|   | 1 | 11275 |
|   | 4.5 | 12915 |
|   | 5.5 | 17630 |
|   | 8 | 13500 |
|   | 10 | 9088 |
|   | 14 | 20295 |
| A | 0 | 3280 |
|   | 1 | 2050 |
|   | 4 | 3485 |
|   | 8 | 3280 |
|   | 10 | 8405 |
|   | 12 | 4510 |
|   | 14 | 8405 |

TABLE 2-continued

| POLYMERIC SPECIMEN | Aging Time at 900° F. (hours) | Wear Rate ($10^{-8}$ $in^3$) |
|---|---|---|
|   | 16 | 6765 |
| C | 0 | 4305 |
|   | 1 | 2050 |
|   | 4 | 1025 |
|   | 8 | 1230 |
|   | 10 | 1025 |
|   | 12 | 1640 |
|   | 14 | 1025 |
|   | 16 | 820 |

Example 3

Cylindrically shaped disks, 1 inch (2.5 cm) diameter×0.5 cm thickness, of Specimens D and B were aged in air at 750° F. (399° C.). Wear rates were measured on unaged and aged samples and are presented in Table 3 and plotted versus aging time in FIG. 3.

TABLE 3

| Material | Aging Time at 750° F. (hours) | Wear Rate ($10^{-8}$ $in^3$) |
|---|---|---|
| POLYMERIC SPECIMEN D | 0 | 2665 |
|   | 8 | 2870 |
|   | 24 | 2460 |
|   | 72 | 2050 |
|   | 144 | 6560 |
|   | 168 | 3280 |
|   | 192 | 17835 |
|   | 336 | 4715 |
| POLYMERIC SPECIMEN B | 0 | 4715 |
|   | 8 | 1640 |
|   | 24 | 1435 |
|   | 72 | 1845 |
|   | 192 | 1845 |
|   | 240 | 2050 |
|   | 408 | 4715 |

Figure 3:
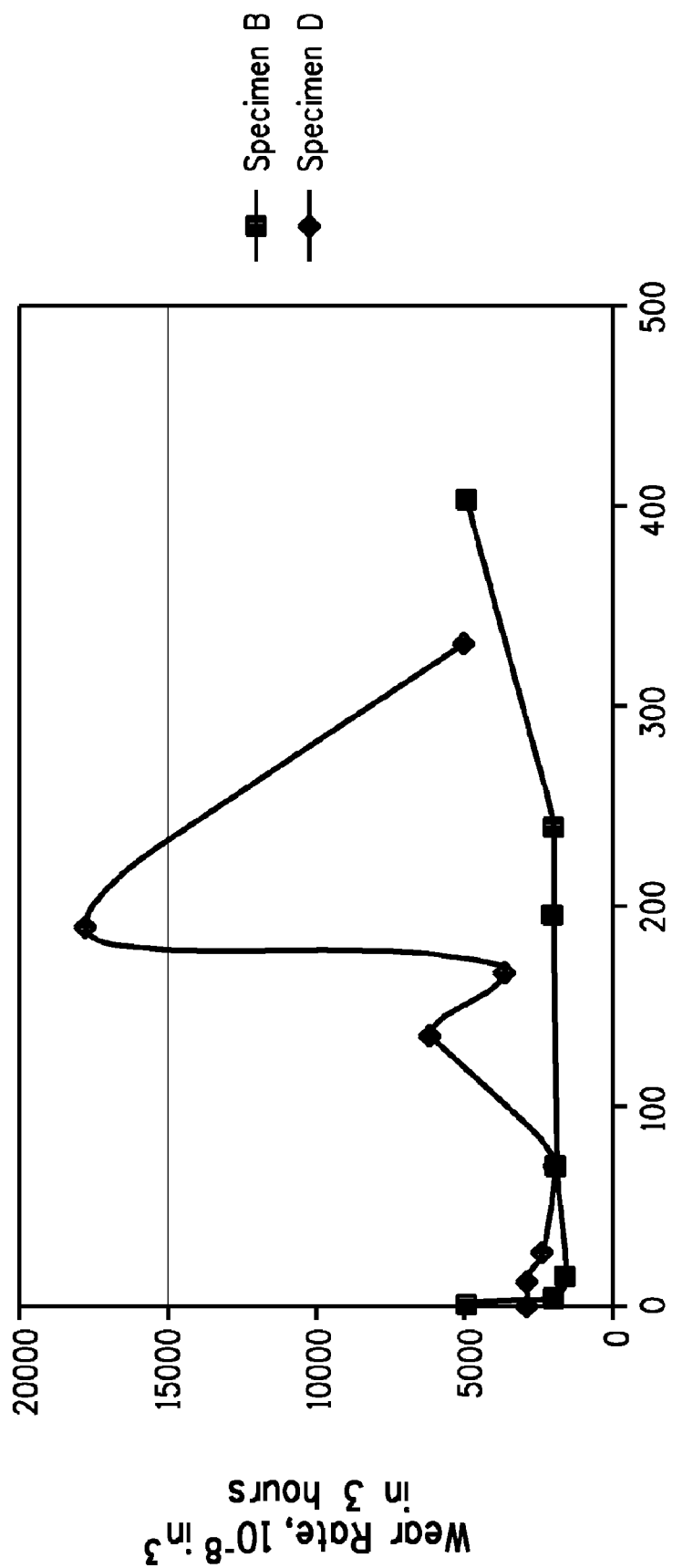
FIG. 3 is a graph of wear rate versus aging time at 900° F. (482° C.) in air for two different Polymeric Specimens, B and D.

In FIG. 3, the area under the curve for polyimide composition Specimen D is clearly larger than the area under the curve for polyimide composition Specimen B. Thus, the performance of parts or shaped specimens made of Specimen D are expected to perform more poorly in high wear conditions at 750° F. (399° C.) in air than parts or shaped specimens made of Specimen B.

Example 4

Figure 4:
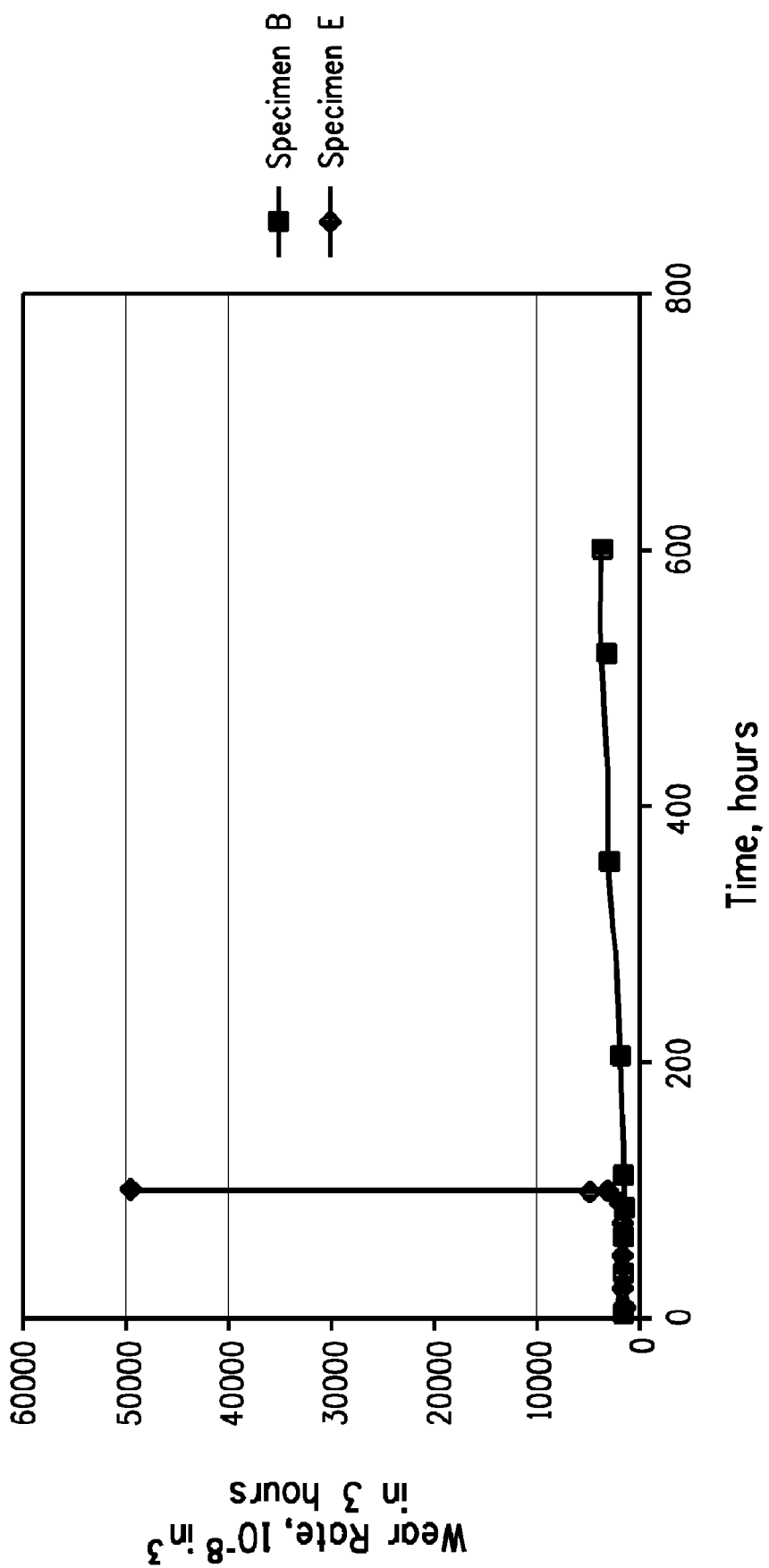
FIG. 4 is a graph of wear rate versus aging time at 900° F. (482° C.) in air for two different Polymeric Specimens, B and E.

Cylindrically shaped disks, 1 inch (2.5 cm) diameter×0.5 cm thickness, of Specimens E and B were aged in air at 750° F. (399° C.). Wear rates were measured on unaged and aged samples and are presented in Table 4 and plotted versus aging time in FIG. 4. At 750° F. (399° C.) in air, Specimen E had failed catastrophically by 97 hours, while after 600 hours, Specimen B showed no signs of catastrophic failure and the wear rate of was only 39% higher than its value at time zero.

TABLE 4

| Material | Aging Time at 750° F. (hours) | Wear Rate ($10^{-8}$ in$^3$) |
|---|---|---|
| POLYMERIC SPECIMEN E | 0 | |
| | 16 | 2489 |
| | 39 | 2231 |
| | 48 | 2646 |
| | 63 | 1720 |
| | 67 | 2394 |
| | 97 | 50000 |
| POLYMERIC SPECIMEN B | 0 | 2056 |
| | 16 | 1791 |
| | 39 | 1946 |
| | 67 | 1704 |
| | 89 | 2117 |
| | 97 | 1829 |
| | 207 | 2105 |
| | 360 | 2333 |
| | 504 | 3187 |
| | 600 | 3378 |

Where a range of numerical values is recited herein, the range includes the endpoints thereof and all the individual integers and fractions within the range, and also includes each of the narrower ranges therein formed by all the various possible combinations of those endpoints and internal integers and fractions to form subgroups of the larger group of values within the stated range to the same extent as if each of those narrower ranges was explicitly recited. Where a range of numerical values is stated herein as being greater than a stated value, the range is nevertheless finite and is bounded on its upper end by a value that is operable within the context of the invention as described herein. Where a range of numerical values is stated herein as being less than a stated value, the range is nevertheless bounded on its lower end by a non-zero value

What is claimed is:

1. A method for evaluating relative wear life of a polymeric specimen, comprising:
   a) providing at least two sets of polymeric specimens, wherein
      (i) each specimen within each set is made of same composition and in same manner, or
      (ii) each specimen within each set is made of same composition as at least one other set and made in a different manner; or
      (iii) each specimen within each set is made of different composition as at least one other set and made in same manner; or
      (iv) each specimen within each set is made of a different composition as at least one other set and made in different manner;
   b) determining wear rate as a function of aging time for each set, by:
      (i) reserving at least one specimen as an unaged control;
      (ii) aging each remaining specimen by heating up to a final temperature of 482° C. under a specified atmosphere and for a specified aging time;
      (iii) measuring the wear rate of the unaged and aged specimens over time;
   wherein the aged specimens have not been subjected to wear prior to aging;
   c) comparing the wear rates as determined in step (b) for each set of specimens.

2. The method of claim 1 wherein the polymeric specimen comprises a filled or unfilled polymer selected from the group consisting of polyimide, polyetherimide, polyketone, polybenzoxazole, polybenzimidazole, polyaramide, polyarylene, polyether sulfone, polyarylene sulfide, polyimidothioether, polyoxamide, polyimine, polysulfonamide, polysulfonimide, polyimidine, polypyrazole, polyisoxazole, polythiazole, polybenzothiazole, polyoxadiazole, polytriazole, polytriazoline, polytetrazole, polyquinoline, polyanthrazoline, polypyrazine, polyquinoxaline, polyquinoxalone, polyquinazolone, polytriazine, polytetrazine, polythiazone, polypyrrone, polyphenanthroline, polycarbosilane, polysiloxane, polyamideimide, and copolymers or blends thereof.

3. The method of claim 1 wherein said polymeric specimen comprises at least one additive.

* * * * *